United States Patent
Wagener et al.

(10) Patent No.: US 9,409,850 B2
(45) Date of Patent: Aug. 9, 2016

(54) METATHESIS DEPOLYMERIZATION USING ACRYLATES

(71) Applicant: UNIVERSITY OF FLORIDA RESEARCH FOUNDATION, INC., Gainesville, FL (US)

(72) Inventors: Kenneth Boone Wagener, Gainesville, FL (US); Michael Schulz, Mainz (DE)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 14/422,740

(22) PCT Filed: Aug. 20, 2013

(86) PCT No.: PCT/US2013/055847
§ 371 (c)(1),
(2) Date: Feb. 20, 2015

(87) PCT Pub. No.: WO2014/031677
PCT Pub. Date: Feb. 27, 2014

(65) Prior Publication Data
US 2015/0232406 A1    Aug. 20, 2015

Related U.S. Application Data

(60) Provisional application No. 61/691,017, filed on Aug. 20, 2012.

(51) Int. Cl.
C07C 51/60 (2006.01)
C07C 57/04 (2006.01)
C07C 67/475 (2006.01)
C08F 236/02 (2006.01)
(Continued)

(52) U.S. Cl.
CPC ............ *C07C 51/60* (2013.01); *C08F 236/02* (2013.01)

(58) Field of Classification Search
CPC ........ C07C 6/04; C07C 57/04; C07C 67/475; C07C 51/60; C08F 8/50
USPC ............ 525/301, 305, 310, 938; 554/27, 30, 554/169, 219
See application file for complete search history.

(56) References Cited

U.S. PATENT DOCUMENTS 5,512,635 A * 4/1996 Nubel .................... C08C 19/28
525/247
7,956,132 B2   6/2011 Arriola et al.

FOREIGN PATENT DOCUMENTS

WO    WO 02-079127    10/2002

OTHER PUBLICATIONS

Biermann, et al, "Acyclic Triene Metathesis Oligo- and Polymerization of High Oleic Sun Flower Oil," Macromol. Chem. Phys. 2010, 211, 854-862.*

(Continued)

*Primary Examiner* — Fred M Teskin
(74) *Attorney, Agent, or Firm* — Saliwanchik, Lloyd & Eisenschenk

(57) ABSTRACT

Olefin metathesis between an acrylate monomer and a polyene comprising molecule or polymer is employed as a method of cross-metathesizing or depolymerizing the molecule. The metathesis reaction forms a telechelic acrylate molecule that is a monomer, oligomer or polymer. The telechelic acrylate molecule can be employed as a monomer for condensation polymerization.

10 Claims, 5 Drawing Sheets

(51) Int. Cl.
C08F 8/50 (2006.01)
B01J 31/12 (2006.01)

(56) References Cited

OTHER PUBLICATIONS

Head, et al., "Synthesis of Membranacin," Synlett, 2004, No. 9, 1437-1439.*

Abbas, M. et al., "As low as reasonably achievable catalyst loadings in the cross metathesis of olefins with ethyl acrylate," *Tetrahedron Letters*, 2011, pp. 2560-2562, vol. 52.

Chatterjee, A.K. et al., "A General Model for Selectivity in Olefin Cross Metathesis," *J. Am. Chem. Soc.*, 2003, pp. 11360-11370, vol. 125.

Choi, T-L, et al., Synthesis of A,B-Alternating Copolymers by Ring-Opening-Insertion-Metathesis Polymerization, *Angew. Chem.*, 2002, pp. 3995-3997, vol. 114.

Craig, S.W. et al., "Highly Efficient Acyclic Diene Metathesis Depolymerization Using a Ruthenium Catalyst Containing a N-Heterocyclic Carbene Ligand," *Macromolecules*, 2001, pp. 7929-7931, vol. 34.

Demel, S. et al., "Alternating Diene Metathesis Polycondensation (ALTMET)—A Versatile Tool for the Preparation of Perfectly Alternating AB Copolymers," *Macromol. Rapid Commun.*, 2003, pp. 636-641, vol. 24.

Ferrie, L. et al., "Acryloyl Chloride: An Excellent Substrate for Cross-Metathesis. A One-Pot Sequence for the Synthesis of Substituted α,β-Unsaturated Carbonyl Derivatives," *Organic Letters*, 2009, pp. 5446-5448, vol. 11, No. 23.

Lanzetta, N. et al., "Polyamides from *trans*-4-Octen-1,8-dioic and *trans*-2-*trans*-6-Octadien-1,8-dioic Acids," *Journal of Polymer Science*, 1973, pp. 913-923, vol. 11.

Marmo, J.C. et al., "Acyclic Diene Metathesis (ADMET) Depolymerization. Synthesis of Mass-Exact Telechelic Polybutadiene Oligomers," *Macromolecules*, 1993, pp. 2137-2138, vol. 26.

Marmo, J.C. et al., "ADMET Depolymerization. Synthesis of Perfectly Difunctional ($f$ =2.0) Telechelic Polybutadiene Oligomers," *Macromolecules*, 1995, pp. 2602-2606, vol. 28.

Morris, C.L. et al., "Oxidative Cyclization Reactions of Trienes and Dienynes: Total Synthesis of Membrarollin," *J. Org. Chem.*, 2009, pp. 981-988, vol. 74.

Schulz, M.D. et al., "Solvent Effects in Alternating ADMET Polymerization," *ACS Macro Lett.*, 2012, pp. 449-451, vol. 1.

Schulz, M.D. et al., "Insertion metathesis depolymization," *Polym. Chem.*, 2013, pp. 3656-3658, vol. 4.

Voigtritter, K. et al., "Rate Enhanced Olefin Cross-Metathesis Reactions: The Copper Iodide Effect," *J. Org. Chem.*, 2011, pp. 4697-4702, vol. 76.

Watson, M.D. et al., "Acyclic Diene Metathesis (ADMET) Depolymerization: Ethenolysis of 1,4-Polybutadiene Using a Ruthenium Complex," *Journal of Polymer Science, Part A: Polymer Chemistry*, 1999, pp. 1857-1861, vol. 37.

Watson, M.D. et al., "Solvent-Free Olefin Metathesis Depolymerization of 1,4-Polybutadiene," *Macromolecules*, 2000, pp. 1494-1496, vol. 33.

Wagener, K.B. et al., "Acyclic diene metathesis depolymerization of elastomers," 1991, pp. 419-425, vol. 12.

* cited by examiner

METATHESIS DEPOLYMERIZATION USING ACRYLATES

CROSS-REFERENCE TO RELATED APPLICATIONS

This application is the U.S. national stage application of International patent application No. PCT/US2013/055847, filed Aug. 20, 2013, which claims the benefit of U.S. Provisional Application Ser. No. 61/691,017, filed Aug. 20, 2012, the disclosures of which are hereby incorporated by reference in their entireties, including any figures, tables, or drawings.

This invention was made with government support under CHE-1058079 awarded by the National Science Foundation. The government has certain rights in the invention.

BACKGROUND OF INVENTION

Olefin metathesis has been used extensively to produce smaller molecules from unsaturated molecules or polymers. Ethenolysis, cross-metathesis with ethylene, has become particularly important, as it has proved useful in making terminal olefins. These processes, however, produce a statistical distribution of products based on the thermodynamic equilibrium of the reaction.

With the development of more effective metathesis catalysts, particularly those with the N-heterocyclic carbene ligand, the use of acrylates and other electron deficient olefins for ethenolysis has become possible. It was observed, however, that the cross-metathesis reaction between an electron-deficient olefin, such as an acrylate, and a relatively electron-rich olefin is essentially irreversible under metathesis conditions. This property of acrylates was utilized to synthesize an alternating copolymer by inserting a diacrylate into a ROMP polymer, see Choi et al., *Angew. Chem.* 2002, 114, 3995-7. In similar fashion, alternating copolymers have been prepared by ADMET by the use of a diacrylate, see Demel et al., *Macromol. Rapid Commun.* 2003, 24, 636-41 and Schulz et al., *Macro Lett.* 2012, 1, 449-51.

There remains a need for the metathesis depolymerization of olefin containing polymers or cross-metathesis with other polyenes to yield useful products. Furthermore, a depolymerization process that: permits formation of useful products; can be carried out with or without employing a solvent; can be carried out over a wide range of pressures or temperatures; does not result in undesired side product; permits incorporation of a variety of desired functionality into a final depolymerization product; and/or permits further modification to a useful product remains a goal.

BRIEF SUMMARY OF THE INVENTION

An embodiment of the invention is directed to a method for controlled depolymerization of a polyene comprising molecule where the polyene comprising molecule is combined with an olefin metathesis catalyst and an acrylic monomer, followed by removing all volatile alkenes that are formed to yield an acrylic diene comprising monomer, oligomer, or polymer. The monomer or oligomer can have two or more acrylic units. The polyene comprising molecule can be a polymer such as polybutadiene, polyisoprene, or other poly(alkylenediene). The polyene comprising molecule can be a polyunsaturated naturally occurring oil, such as castor oil, linseed oil, corn oil, cotton seed oil, peanut oil, soybean oil, sunflower oil, grape seed oil, sesame oil, or hemp oil. The olefin metathesis catalyst can be Grubb's, st generation catalyst, Grubb's $2^{nd}$ generation catalyst, Hoveyda-Grubb's 1st generation catalyst, or Hoveyda-Grubb's $2^{nd}$ generation catalyst, and can be combined with CuI. The acrylic monomer can be an unsubstituted or substituted acrylic acid, acryloyl halide, acrylate, acrylamide, or mono acrylic anhydride. The depolymerization can be carried out in a solvent as needed.

Another embodiment of the invention is directed to the resulting acrylic diene comprising monomer mixture, comprising the structure:

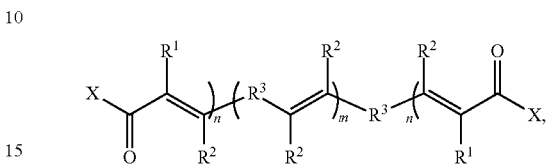

wherein: m>0.01; n≥1; X is OH, Cl, Br, I, OR, NHR, $NR_2$, or RC(O)O; $R^1$ and $R^2$ are independently H, methyl, ethyl, $C_3$ to $C_{14}$ alkyl, $C_6$ to $C_{14}$ aryl, $C_7$ to $C_{14}$ alkylaryl, or $C_7$ to $C_{14}$ arylalkyl, unsubstituted or substituted with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent is optionally further substituted with one or more hydroxy, fluoro, chloro, bromo, or iodo; $R^3$ is a $C_1$ to $C_{14}$ alkylene, $C_6$ to $C_{14}$ arylene, $C_7$ to $C_{14}$ alkylarylene, or any combination thereof connected by ester, amide, ether, amine, or carbonyl linkages, unsubstituted or substituted independently with one or more OH, fluoro, chloro, bromo, iodo, OR, NHR, $NR_2$, or RC(O)O; and R is independently methyl, ethyl, $C_3$ to $C_{14}$ alkyl, $C_6$ to $C_{14}$ aryl, $C_7$ to $C_{14}$ alkylaryl, $C_7$ to $C_{14}$ arylalkyl, unsubstituted or substituted independently with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent on the R is optionally substituted with one or more hydroxy, fluoro, chloro, bromo, or iodo, and wherein, independently, each of the $R^1$ can be situated cis or trans to an adjacent $R^2$.

Another embodiment of the invention is a method of preparing a polymer from the acrylic diene comprising monomer mixture, a complementary comonomer X"—$R^5$—X", where X" is OH, $NH_2$ or NHR, optionally, a solvent and, optionally, a catalyst, to yield a polymer, according to an embodiment of the invention, comprising:

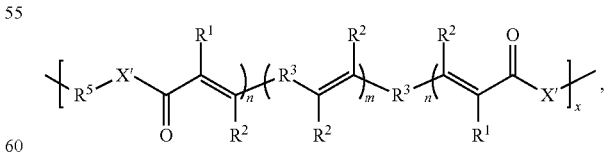

wherein: m>0.01; n≥1; X' is O, NH, or NR; $R^1$ and $R^2$ are independently H, methyl, ethyl, $C_3$ to $C_{14}$ alkyl, $C_6$ to $C_{14}$ aryl, $C_7$ to $C_{14}$ alkylaryl, or $C_7$ to $C_{14}$ arylalkyl, unsubstituted or substituted with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent is optionally further substituted with one or more hydroxy, fluoro, chloro, bromo, or iodo; $R^3$ and $R^5$ are independently $C_1$ to $C_{14}$ alkylene, $C_6$ to $C_{14}$ arylene, $C_7$ to $C_{14}$ alkylarylene, or any combination thereof connected via ester, amide, ether, amine, or carbonyl linkages, unsubstituted or substituted independently with one or more OH, fluoro, chloro, bromo, iodo, OR, NHR, $NR_2$, or RC(O)O; and R is independently methyl, ethyl, $C_3$ to $C_{14}$ alkyl, $C_6$ to $C_{14}$ aryl, $C_7$ to $C_{14}$ alkylaryl, $C_7$ to $C_{14}$ arylalkyl, unsubstituted or substituted independently with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy; wherein the substituent on the R is optionally substituted with one or more hydroxy, fluoro, chloro, bromo, or iodo, and wherein, independently, each of the $R^1$ can be situated cis or trans to an adjacent $R^2$.

DETAILED DISCLOSURE

Figure 1:
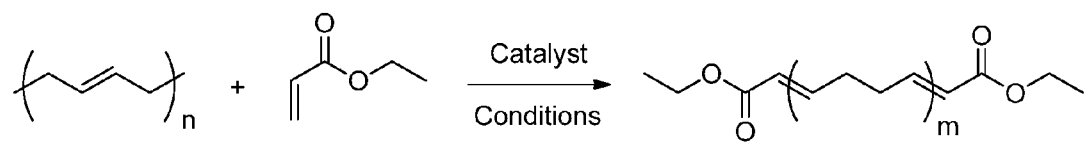
FIG. 1 shows a reaction scheme for the depolymerization of polybutadiene with ethyl acrylate, according to an embodiment of the invention.

Embodiments of the invention are directed to a method of cross-metathesis of an acrylic monomer with a polyene comprising molecule and the cross-metathesis products therefrom, as shown in FIG. 1. The polyene comprising molecule can be any molecule with a plurality of ene units. In one embodiment of the invention the polyene comprising molecule is a polymer and the cross-metathesis products are depolymerization products therefrom, which are molecules that comprise a plurality of acrylic groups. According to an embodiment of the invention, the cross-metathesis method comprises the olefin metathesis of the polyene comprising molecule with an acrylic monomer to form a telechelic monomeric, oligomeric, or polymeric product with a plurality of acrylic groups. The method comprises the mixing of an olefin metathesis catalyst with the polyene comprising molecule and the acrylic monomer where cross-metathesis between the acrylic monomer and the polyene comprising polymer occurs without self-metathesis of the acrylic monomers. The metathesis depolymerization can be carried out with any ratio of acrylic monomers to polyene polymer, ranging from a large excess of acrylic monomer to a large excess of ene-units in the polyene polymer. Polyene comprising polymers can be, but are not limited to, polybutadiene, as shown in FIG. 1, polyisoprene, or other polyalkylene diene, from either a conjugated diene or non-conjugated diene, for example, any polyene comprising polymer prepared by a metathesis polymerization, either ring-opening metathesis polymerization (ROMP) or acyclic diene metathesis polymerization (ADMET). Additional polymers and copolymers that can be used, include, but are not limited to: polychloroprene; polydicyclopentadiene; polyacetylene; copolymers of butadiene and acrylonitrile (NBR); copolymers of butadiene and styrene (SBR); copolymers of butadiene and isoprene; terpolymers of butadiene, acrylonitrile, and butylacrylate; or copolymers of butadiene, acrylonitrile and acrylic acid.

Figure 3:
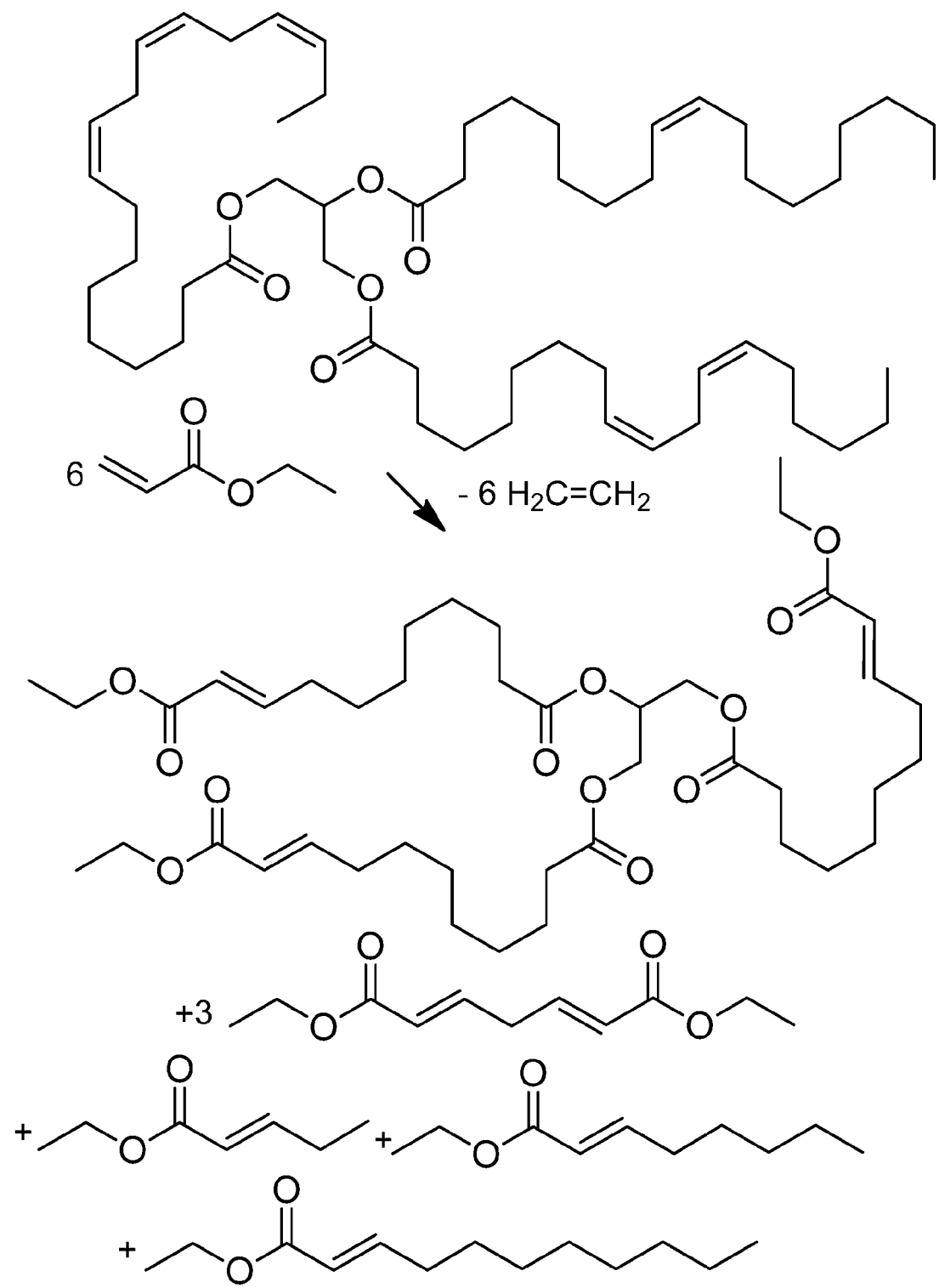
FIG. 3 shows a reaction scheme for the cross-metathesis of the triglyceride in linseed oil and ethyl acrylate, according to an embodiment of the invention.
Figure 4:
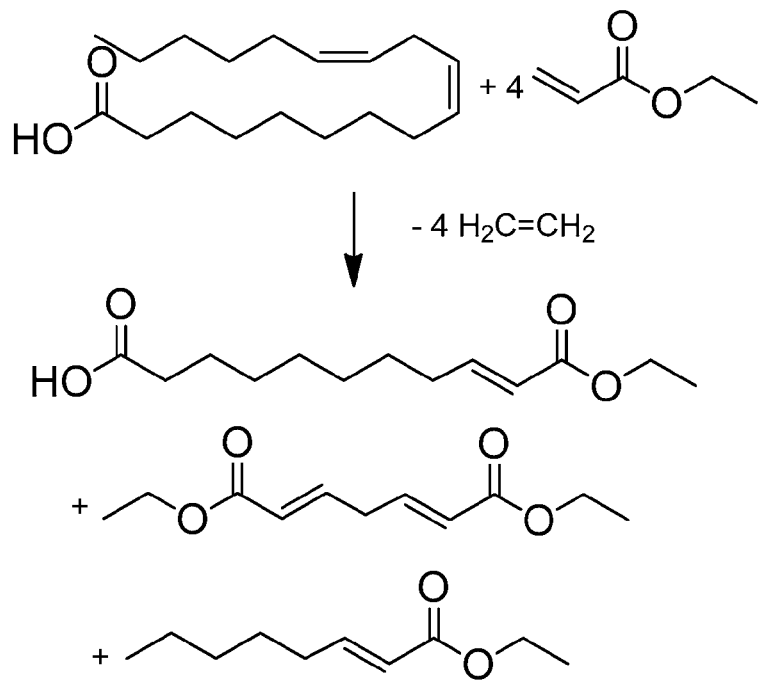
FIG. 4 shows a reaction scheme for the cross-metathesis of linoleic acid with ethyl acrylate, according to an embodiment of the invention.

In another embodiment of the invention the polyene comprising molecule is a naturally occurring oil having a plurality of unsaturation, for example, but not limited to: castor oil or linseed oil, as illustrated in FIG. 3, with plurally unsaturated acid triglycerides; or corn oil, cotton seed oil, peanut oil, soybean oil, sunflower oil, grape seed oil, sesame oil, hemp oil, or other oil with significant portions of linoleic acid, as shown in FIG. 4, or other polyunsaturated fatty acids. In addition to di-acrylate products from these polyene comprising oils, in an embodiment of the invention, mono carboxylic acid-monoene-monoacrylate molecules, as shown in FIG. 4, are prepared that can be used to form condensation polymers such as polyesters, polyamide, or polyamide esters.

Figure 5:
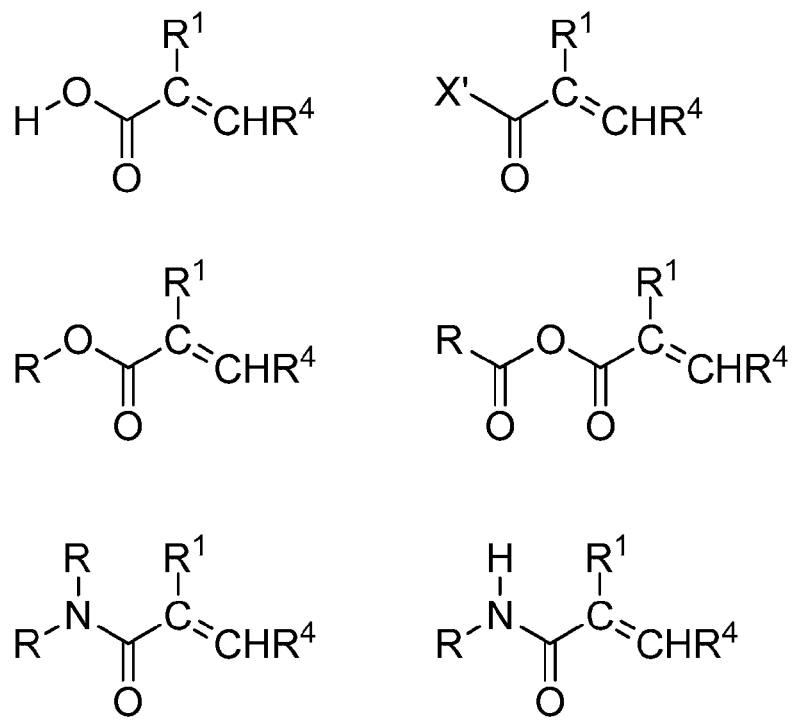
FIG. 5 shows the structure of acrylic esters, amides and anhydrides that can be employed for cross-metathesis, according to embodiments of the invention.

In embodiments of the invention, the acrylic monomer is a mono-ene and can be an unsubstituted or α-substituted acrylic acid, an acryloyl halide, where the halide can be a fluoro, chloro, bromo, or iodo group, an acrylate, an acrylamide, a mono acrylic anhydride, for example, acetic acrylic anhydride, as shown in FIG. 5, or a mixture thereof. The acrylate, acrylamide, or acrylic anhydride, as shown in FIG. 5, can include any non-olefin hydrocarbon groups, R, including, but not limited to, methyl, ethyl, $C_3$ to $C_{14}$ alkyl, $C_6$ to $C_{14}$ aryl, $C_7$ to $C_{14}$ alkylaryl, $C_7$ to $C_{14}$ arylalkyl, or any of these non-olefin hydrocarbon groups substituted with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent can be further substituted with one or more hydroxy, or halo group, and wherein a halo group can be fluoro, chloro, bromo, or iodo. The carbon α to the carbonyl of the acrylate, $R^1$ in FIG. 5, can be H, methyl, ethyl, $C_3$ to $C_{14}$ alkyl, $C_6$ to $C_{14}$ aryl, $C_7$ to $C_{14}$ alkylaryl, $C_7$ to $C_{14}$ arylalkyl, or any of these non-olefin hydrocarbon groups substituted with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent can be further substituted with one or more hydroxy, or halo group, and wherein a halo group can be fluoro, chloro, bromo, or iodo. Any aryl group can be a homoaryl group or heteroaryl group, where one or more carbon atoms of one or more rings can be replaced with any combination of nitrogen, oxygen, or sulfur atoms. The carbon β to the carbonyl can be substituted, indicated as $R^4$ in FIG. 5, with a hydrogen or methyl group, such that a low boiling alkene is formed upon cross-metathesis.

Figure 6:
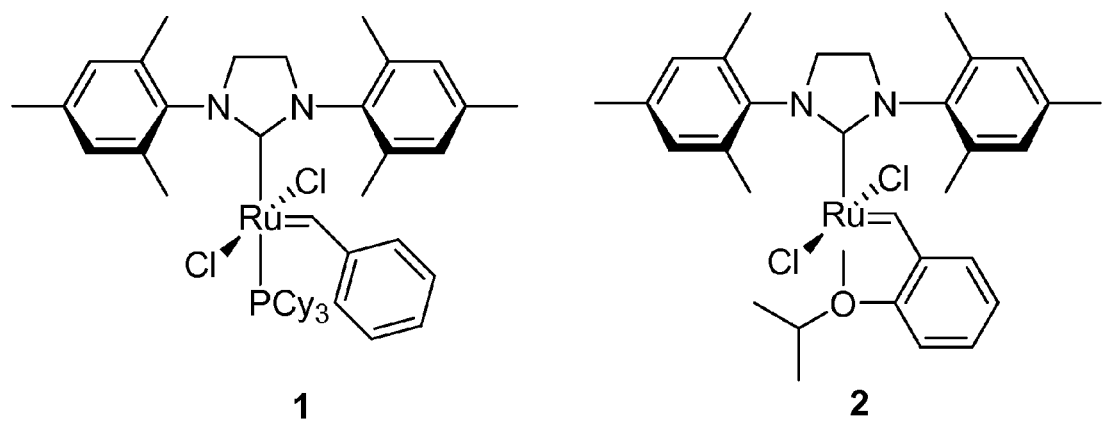
FIG. 6 shows the structures of Grubb's $2^{nd}$ generation catalyst (1) and Hoveyda-Grubb's $2^{nd}$ generation catalyst (2), which can be used for depropagation of the polyene comprising polymer with an acrylic monomer, according to an embodiment of the invention.
Figure 7:
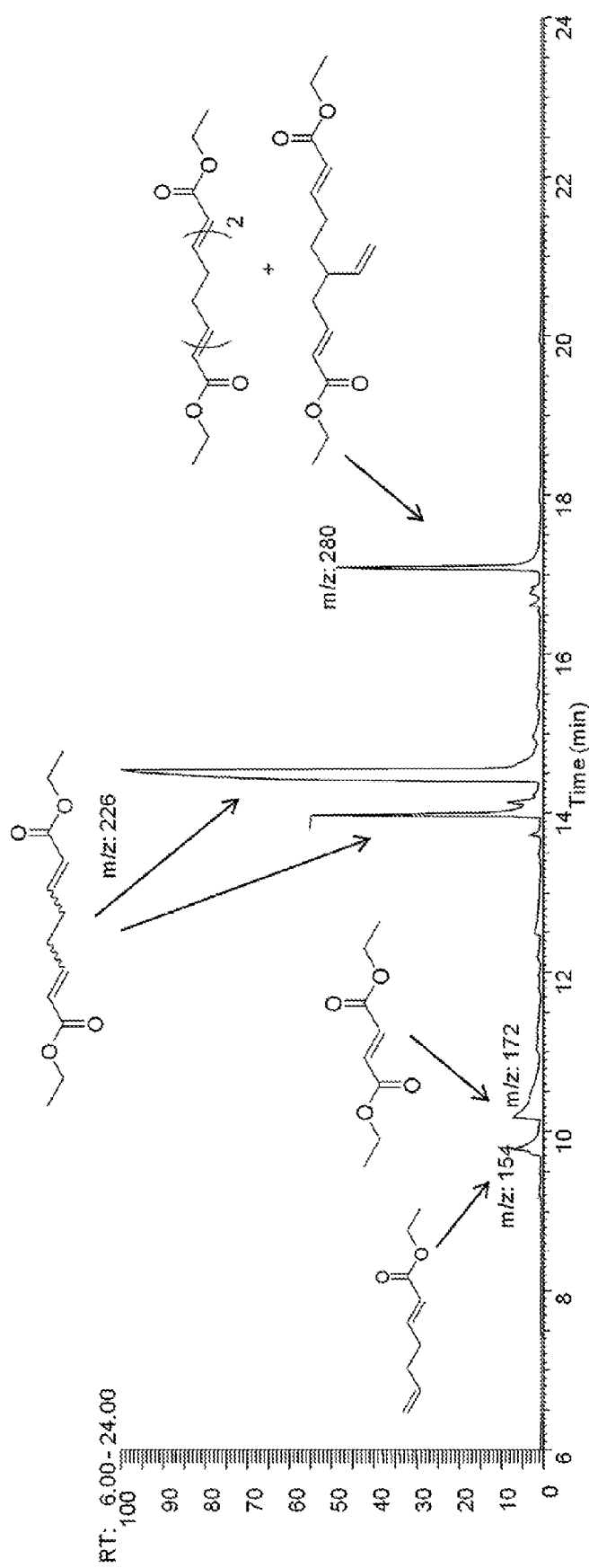
FIG. 7 is a gas chromatograph trace with mass-exact labels obtained by depolymerization of polybutadiene under the conditions of the third entry of Table 1, according to an embodiment of the invention.

Effective metathesis catalysts include ruthenium catalysts with N-heterocyclic carbene ligands, for example, catalysts 1 and 2 of FIG. 6, that permit the cross-metathesis of acrylates or other electron deficient olefins with polyene comprising molecules. In addition to Grubb's $2^{nd}$ generation catalyst (1) and Hoveyda-Grubbs $2^{nd}$ generation catalyst (2), Grubb's $1^{st}$ generation catalyst and Hoveyda-Grubbs 1st generation catalyst can be used to depolymerize the polyene comprising molecules. Other Grubb's type catalysts that can be used include, but are not limited to, dichloro[1,3-bis(2,6-isopropylphenyl)-2-imidazolidinylidene](benzylidene) (tricyclehexylphosphine)ruthenium(II), dichloro[1,3-bis(2,6-isopropylphenyl)-2-imidazolidinylidene](2-isopropoxyphenylmethylene)ruthenium(II), dichloro[1,3-Bis(2-methylphenyl)-2-imidazolidinyl-idene](benzylidene) (tricyclohexyl phosphine)ruthenium(II), dichloro[1,3-bis(2-methylphenyl)-2-imidazolidinylidene](2-isopropoxyphenylmethylene)ruthenium(II), dichloro[1,3-bis(2,4,6-trimethylphenyl)-2-imidazolidinylidene](benzylidene)bis(3-bromopyridine)ruthenium(II), dichloro[1,3-bis(2,4,6-trimethylphenyl)-2-imidazolidinylidene](3-methyl-2-butenylidene)(tricyclohexylphosphine)ruthenium(II), dichloro[1,3-bis(2,4,6-trimethylphenyl)-2-imidazolidinylidene][3-(2-pyridinyl)propylidene]ruthenium(II), dichloro[1,3-bis(2,4,6-trimethylphenyl)-2-imidazol idinylidene][(tricyclohexylphosphoranyl)methylidene]ruthenium(II) tetrafluoroborate, dichloro(3-methyl-2-butenylidene)bis(tricyclohexylphosphine)ruthenium(II), dichloro(3-methyl-2-butenyl-idene)bis(tricyclopentylphosphine)ruthenium(II), or dichloro(tricyclohexylphosphine) [(tricycle-hexylphosphoranyl)methylidene]ruthenium(II) tetrafluoroborate. Alternatively, Schrock's molybdenum and tungsten based catalysts or their derivatives, $WCl_6$, rhenium oxide, or nickel phosphine based catalyst can be used. The cross-metathesis reaction between an acrylate or other electron-deficient and a relatively electron-rich olefin is essentially irreversible under metathesis conditions. In an embodiment of the invention, CuI is included as a component of the metathesis catalyst.

The cross-metathesis can be carried out where the acrylic monomer acts as a solvent, or in the presence of an additional solvent, for example, a hydrocarbon solvent or ether. Almost any solvent can be used, including, but not limited to, dichloromethane, chloroform, dichlorobenzene, chlorobezene, toluene, dichloroethane, acetic acid, methanol, ethanol, tetrahydrofuran, diethyl ether, carbon tetrachloride, water, hexafluoroisopropanol, acrylonitrile, dimethylsulfoxide, dimethylformamide, diglyme, hexanes, cyclohexane, pentane, and heptane. In an embodiment of the invention, an acrylate comprising molecule having a plurality of ene conjugated acrylic groups is prepared by the cross-metathesis reaction. The acrylate comprising molecule is an acrylate comprising monomer mixture, of the structure:

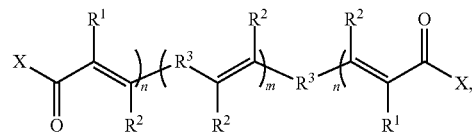

wherein: m>0.01; n≥1; X is OH, Cl, Br, I, OR, NHR, $NR_2$, or RC(O)O; $R^1$ and $R^2$ are independently H, methyl, ethyl, $C_3$ to $C_{14}$ alkyl, $C_6$ to $C_{14}$ aryl, $C_7$ to $C_{14}$ alkylaryl, or $C_7$ to $C_{14}$ arylalkyl, unsubstituted or substituted with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent is optionally further substituted with one or more hydroxy, fluoro, chloro, bromo, or iodo; $R^3$ is a $C_1$ to $C_{14}$ alkylene, $C_6$ to $C_{14}$ arylene, $C_7$ to $C_{14}$ alkylarylene, or any combination thereof connected by ester, amide, ether, amine, or carbonyl linkages, unsubstituted or substituted independently with one or more OH, fluoro, chloro, bromo, iodo, OR, NHR, $NR_2$, or RC(O)O; and R is independently methyl, ethyl, $C_3$ to $C_{14}$ alkyl, $C_6$ to $C_{14}$ aryl, $C_7$ to $C_{14}$ alkylaryl, $C_7$ to $C_{14}$ arylalkyl, unsubstituted or substituted independently with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent on the R is optionally substituted with one or more hydroxy, fluoro, chloro, bromo, or iodo, and wherein, independently, each of the $R^1$ can be situated cis or trans to an adjacent $R^2$. Advantageously, an acrylic monomer mixture is formed from the polyene rather than a pure difunctional monomer having a single repeating unit, m=0, as this can depress crystallization, glass transition temperatures or other thermal or mechanical properties of the acrylic monomer mixture or any polymer formed therefrom.

In an embodiment of the invention, the acrylic monomer mixture can be condensed with a complementary monomer, for example, the acrylic monomer mixture comprising a halide, X=Cl, Br, or I, a carboxylic acid, X=OH, or an ester, X=OR, with a diamine monomer to form a polyamide polymer, or with a diol monomer to form an ester. The complementary monomer can be of the structure:

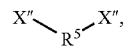

wherein: X" is OH, $NH_2$ or NHR; $R^5$ is $C_1$ to $C_{14}$ alkylene, $C_6$ to $C_{14}$ arylene, $C_7$ to $C_{14}$ alkylarylene, or any combination thereof connected by ester, amide, ether, amine, or carbonyl linkages, unsubstituted or substituted independently with one or more OH, fluoro, chloro, bromo, iodo, OR, NHR, $NR_2$, or RC(O)O; and R is independently methyl, ethyl, $C_3$ to $C_{14}$ alkyl, $C_6$ to $C_{14}$ aryl, $C_7$ to $C_{14}$ alkylaryl, $C_7$ to $C_{14}$ arylalkyl, unsubstituted or substituted independently with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy; wherein the substituent on the R is optionally substituted with one or more hydroxy, fluoro, chloro, bromo, or iodo. The monomer can be a pure compound where all $R^5$ is a single group, or $R^5$ can be a mixture of groups.

The condensation polymerization can be carried out in any manner known for condensation polymerizations with dicarboxylic acids or dicarboxylic acid derivatives, as can be appreciated by those skilled in the art. The condensation polymerization reaction can be carried out with or without a solvent, and can be carried out such that a condensation by-product can be removed from the reaction continuously during the polymerization, as needed. For example, a polyamide can be formed by the polymerization of an acrylic monomer mixture that is a diester with a diamine comonomer, without removal of the alcohol that is formed, whereas a polyester can be prepared for the acrylic monomer mixture that is a diester of a volatile alcohol with a diol comonomer, where the by-product volatile alcohol is distilled from the mixture, alone or as an azeotrope with a component of a solvent used. The polymerization can be catalyzed by any common catalyst, for example, an acid, base, or nucleophilic catalyst, such as a strong protic acid, such as, sulfuric acid, a Lewis acid, such as ferric chloride, or a base, such as a tertiary amine, for example, pyridine or triethylamine, or a nucleophilic catalyst, for example, dimethylaminopyridine. The reaction can be carried out at ambient or elevated temperatures.

Upon reaction of the acrylic monomer mixture with a complementary comonomer, the resulting polymer, according to an embodiment of the invention, can be of the structure:

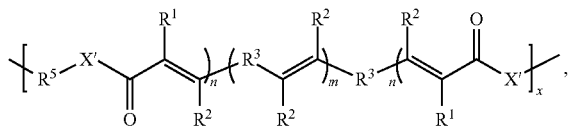

wherein: $m>0.01$; $n \geq 1$; $X'$ is O NH, or NR; $R^1$ and $R^2$ are independently H, methyl, ethyl, $C_3$ to $C_{14}$ alkyl, $C_6$ to $C_{14}$ aryl, $C_7$ to $C_{14}$ alkylaryl, or $C_7$ to $C_{14}$ arylalkyl, unsubstituted or substituted with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent is optionally further substituted with one or more hydroxy, fluoro, chloro, bromo, or iodo; $R^3$ and $R^5$ are independently $C_1$ to $C_{14}$ alkylene, $C_6$ to $C_{14}$ arylene, $C_7$ to $C_{14}$ alkylarylene, or any combination thereof connected by ester, amide, ether, amine, or carbonyl linkages, unsubstituted or substituted independently with one or more OH, fluoro, chloro, bromo, iodo, OR, NHR, $NR_2$, or RC(O)O; and R is independently methyl, ethyl, $C_3$ to $C_{14}$ alkyl, $C_6$ to $C_{14}$ aryl, $C_7$ to $C_{14}$ alkylaryl, $C_7$ to $C_{14}$ arylalkyl, unsubstituted or substituted independently with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy; wherein the substituent on the R is optionally substituted with one or more hydroxy, fluoro, chloro, bromo, or iodo, and wherein, independently, each of the $R^1$ can be situated cis or trans to an adjacent $R^2$.

Methods and Materials

Materials

Ethyl acrylate, acryloyl chloride, 1,6-diaminohexane, and CuI were purchased from Aldrich and used without further purification, unless otherwise noted. Polybutadiene (MW=110 kDa, 97% cis, PDI=2.3) was a gift from Firestone Inc. Alternately, polybutadiene (Mn=125 kDa, 40% cis, PDI=1.2) was used. Grubb's $1^{st}$ generation catalyst, Grubb's $2^{nd}$ generation catalyst (1), Hoveyda-Grubbs 1st generation catalyst, and Hoveyda-Grubbs $2^{nd}$ generation catalyst (2) were provided by Materia Inc. Acrylates were stored with the included inhibitor methylethylhydroquinone (MEHQ) and used without purification.

Instrumentation $^1$H NMR (300 MHz) and $^{13}$C NMR (75 MHz) spectra were recorded on a Varian Mercury 300 spectrometer. Chemical shifts for $^1$H and $^{13}$C NMR were referenced to residual signals from $CDCl_3$ ($^1$H 7.25 ppm and $^{13}$C 77.00 ppm).

Depolymerization

A flame-dried Schlenk tube was charged with polybutadiene (0.5 g, 9.25 mmol repeat unit, ~0.03 g segments) and 0.1 mmol catalyst under argon. 2 mL (18.8 mmol). Ethyl acrylate was injected into the polymer-catalyst mixture. The reaction mixture was stirred at 50° C. Progress of the reaction was monitored by removing aliquots for analysis by $^1$H NMR.

As can be seen in Table 1, below, catalysts 1, 2, and 1/CuI depolymerized polybutadiene at 50° C. under Argon. Conversion is indicated by the value of m, where a value of 1 indicates complete conversion to a single butadiene unit between the acrylates. Conversion is reflected by the degree of polymerization of the resulting polymer, oligomer, or monomer that is formed upon cross-metathesis in view of the amount of acrylic monomer used, as in the reaction shown in FIG. 1. Under appropriate conditions, catalysts 2 and 1/CuI promoted nearly complete depolymerization. A significant difference in the efficacy of 1 was observed upon the addition of CuI. The improved efficiency afforded to catalyst 1 by CuI extended the catalyst's use to an air atmosphere, where significant depolymerization occurred in the presence of air in spite of the air-sensitivity commonly attributed to the catalysts, as the depolymerization of polybutadiene occurred to a high degree with 2 and 1/CuI. Catalyst loading of 0.1 mol % indicated a high activity for depolymerization of polybutadiene, with the depolymerization proceeding nearly to completion using 1/CuI.

TABLE 1

Depolymerization

| Catalyst | Mol % Catalyst[1] | Conditions | Time (hours) | m |
|---|---|---|---|---|
| 2 | 0.1 | 50° C., Ar | 1 | 1.78 |
| 2 | 0.1 | 50° C., Ar | 24 | 1.76 |
| 2 | 0.5 | 50° C., Ar | 24 | 1.09 |
| 2 | 1 | 50° C., Ar | 24 | 1.09 |
| 2 | 1 | 50° C., Ar | 42 | 1.09 |
| 2 | 0.5[2] | 50° C., Ar | 24 | 1.15 |
| 2 | 1 | 50° C., Ar | 1 | 1.39 |
| 2 | 1 | RT, Air | 26 | 5.45 |
| 2 | 1 | RT, Air | 1 | 6.31 |
| 1 | 0.5 | 50° C., Ar | 120 | 27.97 |
| 1/CuI | 1 | 50° C., Ar | 26 | 1.015 |

TABLE 1-continued

Depolymerization

| Catalyst | Mol % Catalyst[1] | Conditions | Time (hours) | m |
|---|---|---|---|---|
| 1/CuI | 0.5 | 50° C., Ar | 24 | 1.015 |
| 1/CuI | 0.1 | 50° C., Ar | 1 | 1.16 |
| 1/CuI | 0.1 | 50° C., Ar | 24 | 1.16 |
| 1/CuI | 1 | RT, Ar | 42 | 1.12 |
| 1/CuI | 0.5 | RT, Ar | 42 | 1.12 |
| 1/CuI | 0.5 | RT, Air | 2 | 4.49 |
| 1/CuI | 0.5 | RT, Air | 47 | 4.49 |
| 1/CuI | 0.5 | 50° C., Air | 20 | 1.36 |

[1]relative to polybutadiene repeating units,
[2]alternate polydutadiene having 40% cis content.

The depolymerization was monitored by $^1$H NMR, with aliquots taken at 1, 2, 4, and 24 hour into the reaction for analysis. As can be seen from Table 1, above, the reaction is nearly complete in less than one hour, for all levels of catalyst.

Figure 2:
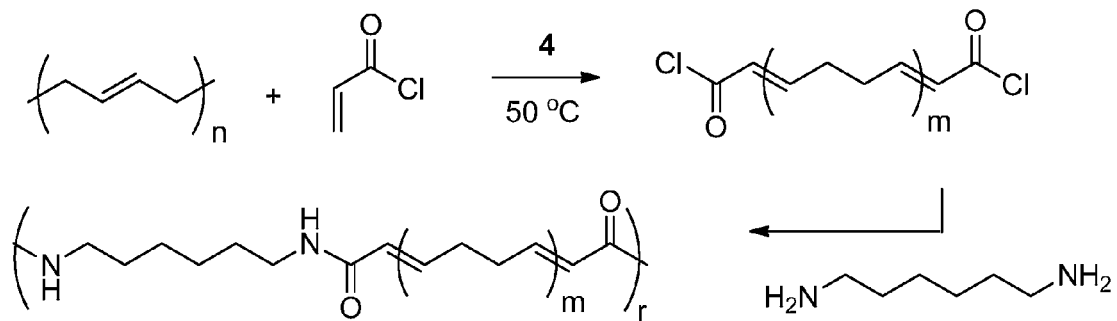
FIG. 2 shows a reaction scheme for the depropagation of polybutadiene with acryloyl chloride, according to an embodiment of the invention, and the subsequent preparation of a polyamide from the α,ω-di acid chloride formed upon depolymerization.

The depolymerization of polybutadiene was carried out using catalyst 2 and acryloyl chloride as the acrylic monomer. The resulting α,ω-diacid chloride oligobutadiene was used to prepare a polyamide with 1,6-diaminohexane, as indicated in FIG. 2, the α,ω-diacid chloride oligobutadiene had an average of four diene repeating units (m=4 in FIG. 2) by NMR analysis. The resulting polyamide was largely in the form of an intractable solid with a glass transition temperature, $T_g$, of 82.6° C.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method of depolymerization comprising:
providing a polyene comprising molecule;
providing an olefin metathesis catalyst, wherein the olefin metathesis catalyst further comprises CuI;
providing an acrylic monomer;
combining the polyene comprising molecule with the olefin metathesis catalyst and the acrylic monomer; and
removing an alkene; wherein an acrylic diene comprising monomer, oligomer, or polymer results, wherein the acrylic diene comprising monomer mixture has a plurality of acrylic units on each of the acrylic diene comprising monomers.

2. The method of claim 1, wherein the polyene comprising molecule is polybutadiene, polyisoprene, or other polyalkylene diene.

3. The method of claim 1, wherein the polyene comprising molecule is a polyunsaturated naturally occurring oil.

4. The method of claim 3, wherein the polyunsaturated naturally occurring oil is castor oil, linseed oil, corn oil, cotton seed oil, peanut oil, soybean oil, sunflower oil, grape seed oil, sesame oil, or hemp oil.

5. The method of claim 1, wherein the olefin metathesis catalyst comprises Grubb's 1$^{st}$ generation catalyst, Grubb's 2$^{nd}$ generation catalyst, Hoveyda-Grubb's 1st generation catalyst, or Hoveyda-Grubb's 2$^{nd}$ generation catalyst.

6. The method of claim 1, wherein the acrylic monomer is an unsubstituted or substituted acrylic acid, acryloyl halide, acrylate, acrylamide, or mono acrylic anhydride.

7. The method of claim 1, further comprising a solvent.

8. A polymer, comprising:

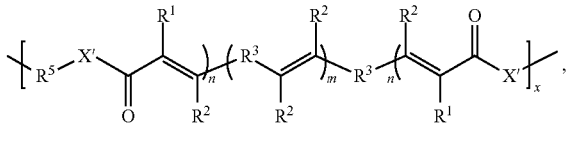

wherein: m>0.01; n≥1; X' is O NH, or NR; $R^1$ and $R^2$ are independently H, methyl, ethyl, $C_3$ to $C_{14}$ alkyl, $C_6$ to $C_{14}$ aryl, $C_7$ to $C_{14}$ alkylaryl, or $C_7$ to $C_{14}$ arylalkyl, unsubstituted or substituted with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent is optionally further substituted with one or more hydroxy, fluoro, chloro, bromo, or iodo; $R^3$ and $R^5$ are independently $C_1$ to $C_{14}$ alkylene, $C_6$ to $C_{14}$ arylene, $C_7$ to $C_{14}$ alkylarylene, or any combination thereof connected by ester, amide, ether, amine, or carbonyl linkages, unsubstituted or substituted independently with one or more OH, fluoro, chloro, bromo, iodo, OR, NHR, NR$_2$, or RC(O)O; and R is independently methyl, ethyl, $C_3$ to $C_{14}$ alkyl, $C_6$ to $C_{14}$ aryl, $C_7$ to $C_{14}$ alkylaryl, $C_7$ to $C_{14}$ arylalkyl, unsubstituted or substituted independently with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy; wherein the substituent on the R is optionally substituted with one or more hydroxy, fluoro, chloro, bromo, or iodo, and wherein, independently, each of the $R^1$ can be situated cis or trans to an adjacent $R^2$, and wherein x is greater than 3.

9. The polymer of claim 8, wherein X' is O, NH, or NR, R is methyl or ethyl, m is 0.015 to 34.57, n is 1, and $R^1$ is H, $R^2$ is H, and $R^3$ is $C_2$ alkylene, and $R^5$ is $C_6$ to $C_{12}$ alkylene or $C_6$ arylene.

10. A method of preparing a polymer according to claim 8, comprising:
providing a acrylic diene comprising monomer mixture, comprising the structure:

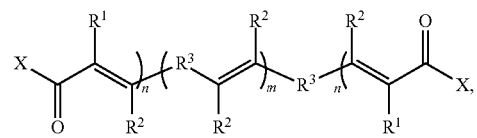

wherein: m>0.01; n≥1; X is OH, Cl, Br, I, OR, NHR, NR$_2$, or RC(O)O; $R^1$ and $R^2$ are independently H, methyl, ethyl, $C_3$ to $C_{14}$ alkyl, $C_6$ to $C_{14}$ aryl, $C_7$ to $C_{14}$ alkylaryl, or $C_7$ to $C_{14}$ arylalkyl, unsubstituted or substituted with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent is optionally further substituted with one or more hydroxy, fluoro, chloro, bromo, or iodo; $R^3$ is a $C_1$ to $C_{14}$ alkylene, $C_6$ to $C_{14}$ arylene, $C_7$ to $C_{14}$ alkylarylene, or any combination thereof connected by ester, amide, ether, amine, or carbonyl linkages, unsubstituted or substituted independently with one or more OH, fluoro, chloro, bromo, iodo, OR, NHR, $NR_2$, or RC(O)O; and R is independently methyl, ethyl, $C_3$ to $C_{14}$ alkyl, $C_6$ to $C_{14}$ aryl, $C_7$ to $C_{14}$ alkylaryl, $C_7$ to $C_{14}$ arylalkyl, unsubstituted or substituted independently with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy, wherein the substituent on the R is optionally substituted with one or more hydroxy, fluoro, chloro, bromo, or iodo;

providing a complementary comonomer of the structure:

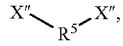

wherein: X" is OH, $NH_2$ or NHR; $R^5$ is $C_1$ to $C_{14}$ alkylene, $C_6$ to $C_{14}$ arylene, $C_7$ to $C_{14}$ alkylarylene, or any combination thereof connected by ester, amide, ether, amine, or carbonyl linkages, unsubstituted or substituted independently with one or more OH, fluoro, chloro, bromo, iodo, OR, NHR, $NR_2$, or RC(O)O; and R is independently methyl, ethyl, $C_3$ to $C_{14}$ alkyl, $C_6$ to $C_{14}$ aryl, $C_7$ to $C_{14}$ alkylaryl, $C_7$ to $C_{14}$ arylalkyl, unsubstituted or substituted independently with one or more hydroxy, halo, $C_1$-$C_{14}$ alkoxy, $C_6$ to $C_{14}$ aryloxy, $C_7$ to $C_{14}$ alkylaryloxy, $C_7$ to $C_{14}$ arylalkoxy, cyano, alkylcarboxy, arylcarboxy, amino, $C_1$-$C_{14}$ alkylamino, $C_6$-$C_{14}$ arylamino, $C_2$-$C_{14}$ dialkylamino, $C_{12}$-$C_{16}$ diarylamino, $C_7$-$C_{14}$ alkylarylamino, carboxyhydroxy, $C_1$-$C_{14}$ alkoxycarboxy, $C_6$ to $C_{14}$ aryloxycarboxy, $C_1$-$C_{14}$ alkylcarboxyoxy, or $C_6$ to $C_{14}$ arylcarboxyoxy; wherein the substituent on the R is optionally substituted with one or more hydroxy, fluoro, chloro, bromo, or iodo;

combining the monomer mixture, the comonomer, and optionally a solvent into a polymerization mixture;

optionally adding a catalyst to the polymerization mixture; and optionally promoting polymerization by heating and/or removal of a condensation product.

* * * * *